(12) United States Patent
Feist et al.

(10) Patent No.: US 9,212,947 B2
(45) Date of Patent: Dec. 15, 2015

(54) MEASUREMENT, COATING AND MONITORING SYSTEM AND METHOD

(75) Inventors: Jörg Peter Feist, London (GB); John Rayment Nicholls, Great Horwood (GB); Michael James Fraser, Brussels (BE); Andrew Lawrence Heyes, London (GB)

(73) Assignee: NEW STS LIMITED, Surrey (GB)

( * ) Notice: Subject to any disclaimer, the term of this patent is extended or adjusted under 35 U.S.C. 154(b) by 1689 days.

(21) Appl. No.: 12/064,666

(22) PCT Filed: Aug. 24, 2006

(86) PCT No.: PCT/GB2006/003176
§ 371 (c)(1),
(2), (4) Date: Aug. 20, 2008

(87) PCT Pub. No.: WO2007/023292
PCT Pub. Date: Mar. 1, 2007

(65) Prior Publication Data
US 2009/0122832 A1    May 14, 2009

(30) Foreign Application Priority Data

Aug. 24, 2005  (GB) .................................. 0517288.7
Aug. 24, 2005  (GB) .................................. 0517289.5

(51) Int. Cl.
*G01K 11/20*   (2006.01)
*G01K 11/32*   (2006.01)
(Continued)

(52) U.S. Cl.
CPC . *G01J 1/58* (2013.01); *C23C 4/105* (2013.01); *C23C 4/12* (2013.01); *F01D 5/288* (2013.01);
(Continued)

(58) Field of Classification Search
CPC ................. G01J 5/08; G01J 5/52; G01J 1/58; G01J 5/0003; G01K 11/20; G01K 11/3213; G01K 11/12; G01K 11/32; G01K 2213/00
USPC ............. 374/1, 2, 3, 120, 121, 129, 124, 137, 374/166, 167, 161–162, 141, 100, 107, 112, 374/102, 103; 356/43; 250/338.1; 385/12, 385/115
See application file for complete search history.

(56) References Cited

U.S. PATENT DOCUMENTS 3,575,873 A * 4/1971 Carver et al. ............ 252/301.36
4,061,578 A * 12/1977 Kleinerman .................. 250/330
(Continued)

FOREIGN PATENT DOCUMENTS

EP   0599208   6/1994
EP   0863396   9/1998
(Continued)

OTHER PUBLICATIONS

International Search Report for corresponding application No. PCT/GB2006/003176, Jan. 26, 2007.
(Continued)

*Primary Examiner* — Gail Kaplan Verbitsky
(74) *Attorney, Agent, or Firm* — Renner, Otto, Boisselle & Sklar, LLP

(57) ABSTRACT

A measurement system for and method of measuring thicknesses of coatings as applied to objects and a coating system and method for. coating objects, in particular three-dimensional objects, with coatings, in particular thermal barrier coatings (TBCs), and a monitoring system for and method of monitoring a state of a thermal barrier coating (TBC) as applied to an object which is exposed to a high-temperature environment, and a TBC for use with the same.

6 Claims, 7 Drawing Sheets

(51) Int. Cl.

| | | |
|---|---|---|
| *G01J 1/00* | (2006.01) | |
| *G01J 1/58* | (2006.01) | |
| *C23C 4/10* | (2006.01) | |
| *C23C 4/12* | (2006.01) | |
| *F01D 5/28* | (2006.01) | |
| *F01D 21/00* | (2006.01) | |
| *G01B 11/06* | (2006.01) | |
| *G01N 21/64* | (2006.01) | |
| *G01N 21/84* | (2006.01) | |

(52) U.S. Cl.
CPC .......... *F01D 21/003* (2013.01); *G01B 11/0658* (2013.01); *G01N 21/64* (2013.01); *G01N 21/8422* (2013.01); *F05D 2230/90* (2013.01); *F05D 2260/80* (2013.01); *G01N 2021/6491* (2013.01)

(56) References Cited

U.S. PATENT DOCUMENTS

| | | | | |
|---|---|---|---|---|
| 4,774,150 | A | | 9/1988 | Amano et al. |
| 4,789,992 | A | * | 12/1988 | Wickersheim et al. ....... 374/161 |
| 4,885,633 | A | * | 12/1989 | Buck ............................ 348/135 |
| 5,112,137 | A | * | 5/1992 | Wickersheim et al. ....... 374/131 |
| 5,183,338 | A | * | 2/1993 | Wickersheim et al. ....... 374/131 |
| 5,219,226 | A | * | 6/1993 | James ........................... 374/124 |
| 5,255,980 | A | * | 10/1993 | Thomas et al. ............... 374/161 |
| 5,272,340 | A | * | 12/1993 | Anbar ........................... 250/332 |
| 6,368,672 | B1 | | 4/2002 | Thompson et al. ........... 427/452 |
| 6,575,620 | B1 | * | 6/2003 | Banaszak et al. .................. 374/4 |
| 6,648,506 | B2 | | 11/2003 | McGrath et al. .............. 374/161 |
| 6,804,622 | B2 | * | 10/2004 | Bunker et al. ................ 702/134 |
| 6,943,357 | B2 | * | 9/2005 | Srivastava et al. ......... 250/458.1 |
| 7,507,022 | B2 | * | 3/2009 | Bird ............................... 374/161 |
| 7,556,851 | B2 | * | 7/2009 | Lampenscherf ............... 428/134 |
| 7,632,012 | B2 | * | 12/2009 | Twerdochlib ................. 374/129 |
| 7,887,234 | B2 | * | 2/2011 | Jonnalagadda et al. ...... 374/124 |
| 8,192,077 | B2 | * | 6/2012 | Twerdochlib ................. 374/129 |
| 2002/0006153 | A1 | * | 1/2002 | Ranson et al. ................ 374/161 |
| 2002/0126732 | A1 | * | 9/2002 | Shakouri et al. .............. 374/130 |
| 2002/0186748 | A1 | * | 12/2002 | Yates et al. .................... 374/161 |
| 2003/0024269 | A1 | * | 2/2003 | Shepard et al. ............. 65/29.18 |
| 2004/0138850 | A1 | * | 7/2004 | Nakakita et al. .............. 702/130 |
| 2004/0179575 | A1 | | 9/2004 | Markham |
| 2006/0140248 | A1 | * | 6/2006 | Gotthold et al. ............... 374/161 |
| 2006/0188000 | A1 | * | 8/2006 | Bird ............................... 374/161 |
| 2007/0015283 | A1 | * | 1/2007 | Choy et al. ........................ 436/2 |
| 2007/0189359 | A1 | * | 8/2007 | Chen et al. .................... 374/161 |
| 2008/0225926 | A1 | * | 9/2008 | Gotthold et al. .............. 374/131 |
| 2009/0296770 | A1 | * | 12/2009 | Kinugasa et al. ................ 374/1 |
| 2009/0312956 | A1 | * | 12/2009 | Zombo et al. ................... 702/34 |

FOREIGN PATENT DOCUMENTS

| | | |
|---|---|---|
| EP | 1105550 | 3/2003 |
| EP | 1318211 | 6/2003 |
| GB | 1191476 | 5/1970 |
| JP | 58005622 A * | 1/1983 |
| JP | 2005146291 | 6/2005 |
| WO | 95/30890 | 11/1995 |
| WO | 2005/019784 | 3/2005 |

OTHER PUBLICATIONS

Eldridge, J I et al., "Depth-Penetrating Temperature Measurements of Thermal Barrier Coatings Incorporating Thermographic Phosphors", Journal of Thermal Spray Technology, vol. 13(1), Mar. 2004, pp. 44-50.

* cited by examiner

MEASUREMENT, COATING AND MONITORING SYSTEM AND METHOD

This application is a national phase of International Application No. PCT/GB2006/003176 filed Aug. 24, 2006 and published in the English language.

The present invention relates to a measurement system for and method of measuring thicknesses of coatings as applied to objects and a coating system and method for coating objects, in particular three-dimensional objects, with coatings, in particular thermal barrier coatings (TBCs), and a monitoring system for and method of monitoring a state of a thermal barrier coating (TBC) as applied to an object which is exposed to a high-temperature environment, and a TBC for use with the same.

The coating of objects, for example, by spraying techniques, is well established, with the thickness of a coating being dictated by the coating parameters. In existing coating systems, a coating of a required thickness is obtained by control of the coating parameters. For example, in a spraying technique which operates under predetermined process conditions and provides for a coating thickness of 1 µm in a single pass, a coating of 5 µm would be achieved by performing five passes at those process conditions.

One problem associated with coating systems is that the thickness of a coating can vary significantly from object to object, and, for some coatings, such as TBCs, the thickness and continuity of the coating is critical to the performance of the object.

The present inventors have recognized that the improved coating of objects can be achieved through the provision of a luminescent material at the surface of an object which is to be coated, and detecting the luminescence emission from the coated object, where the intensity of the luminescence emission provides for a determination of the thickness of the coating.

Thickness monitoring techniques which utilize a fluorescent material for the monitoring of the thickness of a coating have been revealed in searches from other fields of art. Examples include EP-A-0599208 and EP-A-1318211. Notwithstanding that these techniques relate to entirely different fields of art, which a person skilled in the art would have had no motivation to consider, these techniques will be briefly considered below.

EP-A-0599208 discloses a co-extrusion process in which the core layer includes a fluorescent dye, which allows for a determination of the effectiveness of the outer coating of an extruded product by monitoring for fluorescence from the core layer. Where fluorescence is detected, the outer layer is determined not to have the adequate thickness, and the extruded product is not acceptable. Such a co-extrusion process is entirely unrelated to the present invention, which provides for the measurement and control of the thickness of a coating which is progressively deposited on an object, in particular a TBC.

EP-A-1318211 discloses a monitoring process which provides for the monitoring of the thickness of a deposit which deposits on the sidewall of a processing chamber by monitoring the fluorescence emission from a fluorescent layer, and allows for a determination as to when the processing chamber requires cleaning. There is no disclosure or suggestion of the measurement and control of the thickness of a coating which is progressively deposited on an object, in particular a TBC, and certainly no suggestion of the mapping of the thickness profile of a coated object. As should be understood, the thickness and continuity of TBCs is critical, as otherwise catastrophic failure of the coated object will occur.

In one aspect the present invention provides a measurement system for measuring thicknesses of coatings as applied to objects, the system comprising: a support unit for supporting an object which includes a coating and a luminescent material beneath the coating; a detector unit including a detector for detecting a luminescence signal from the luminescent material, wherein an intensity of the luminescence signal represents the thickness of the coating; and a determination unit for determining the thickness of the coating from the intensity of the luminescence signal as detected by the detector of the detector unit.

In another aspect the present invention provides a method of measuring thicknesses of coatings as applied to objects, the method comprising the steps of: supporting an object which includes a coating and a luminescent material beneath the coating; detecting a luminescence signal from the luminescent material, wherein an intensity of the luminescence signal represents the thickness of the coating; and determining the thickness of the coating from the intensity of the luminescence signal as detected by the detector of the detector unit.

In a further aspect the present invention provides a coating system for coating objects, the system comprising: a support unit for supporting an object to be coated; an applicator unit including an applicator for applying a coating material to a surface of the object to form a coating on the object; a detector unit including a detector for detecting a luminescence signal from the surface of the object, wherein an intensity of the luminescence signal represents a thickness of the applied coating; and a determination unit for determining the thickness of the coating from the intensity of the luminescence signal as detected by the detector of the detector unit.

In a still further aspect the present invention provides a method of coating objects, the method comprising the steps of: supporting an object to be coated; applying a coating material to a surface of the object to form a coating on the object; detecting a luminescence signal from the surface of the object, wherein an intensity of the luminescence signal represents a thickness of the coating; and determining the thickness of the coating from the intensity of the detected luminescence signal.

Another feature of the present invention relates to the failure of TBCs, which often occurs as a result of de-lamination from the underlying objects, which de-lamination usually is a progressive failure which arises from localized blisters.

The present inventors have recognized that it is possible to monitor TBCs for the generation of such blisters, and thus provide for an early warning to the possible failure of the associated objects, which enables the associated machinery which incorporates the objects to be taken out of service and thereby prevent potentially catastrophic failure of that machinery.

There are existing techniques, such as disclosed in JP-A-2005-146291, which utilize a luminescent coating to provide for detection of physical damage in a TBC, either through erosion or de-lamination through peeling, but none of these techniques provide for the monitoring of the generation of blisters which occur at the interface of TBCs and the coated objects, which typically are turbine blades.

JP-A-2005-146291 discloses a system and method which detects physical damage to a TBC by incorporating a luminescent coating in the TBC and monitoring the exhaust gas stream for the presence of luminescent particles, which are indicative of physical damage to the TBC. Such monitoring of TBCs does not allow for detection of blisters which occur at the interface of the TBCs ahead of the disintegration of the luminescent coating. It is a particular aspect of the present invention that blisters be achieved ahead of dis-integration of the luminescent coating, which allows the coated object to be removed from service and re-furbished, instead of being scrapped, as would otherwise ordinarily occur following catastrophic failure.

In one aspect the present invention provides a monitoring system for monitoring a state of a thermal barrier coating comprising a first, lower luminescent coating on a surface of an object and a second, upper structural coating on the lower coating, the system comprising: a detector unit including a detector for detecting a luminescence signal from the luminescent coating, wherein the detected luminescence signal is representative of a temperature of the luminescent coating; and a monitoring unit for monitoring the detected luminescence signal for at least one characteristic which is representative of a localized region of raised or reduced temperature in the luminescent coating, and providing a control indication on detecting the at least one characteristic.

In another aspect the present invention provides a method of monitoring a state of a thermal barrier coating comprising a first, lower luminescent coating on a surface of an object and a second, upper structural coating on the lower coating, the method comprising the steps of: detecting a luminescence signal from the luminescent coating, wherein the detected luminescence signal is representative of a temperature of the luminescent coating; and monitoring the detected luminescence signal for at least one characteristic which is representative of a localized region of raised or reduced temperature in the luminescent coating.

In a further aspect the present invention provides an object coated with a thermal barrier coating comprising a first, lower luminescent coating on a surface of the object and a second, upper main coating on the lower coating, wherein the main coating has a thickness substantially greater than that of the luminescent coating.

In a still further aspect the present invention provides a system and method for pyrometrically determining a temperature of an object which incorporates or is coated with a luminescent material, typically a thermographic phosphor, by referencing the detected signal of a pyrometer to the temperature as determined from the luminescence emission from the luminescent material.

A particular disadvantage of pyrometers, as employed in high-temperature environments, arises from the fact that the manifestation of surface artefacts, for example, surface deposits, means that a precise determination of the temperature of an object is not possible, but the present inventors have recognized that this is overcome by referencing the pyrometrically-determined temperature to the temperature as determined from a luminescence emission.

Preferred embodiments of the present invention will now be described hereinbelow by way of example only with reference to the accompanying drawings, in which:

FIG. 1 schematically illustrates a coating system in accordance with a preferred embodiment of the present invention;

FIGS. 2(a) to (e) illustrate the steps in coating a component with a structural coating using the coating system of FIG. 1, when operative in accordance with one embodiment of the present invention;

FIG. 3 illustrates a plot representing the relationship of coating thickness to the intensity of the detected luminescence signal;

FIGS. 4(a) to (e) illustrate the steps in coating a component with a structural coating using the coating system of FIG. 1, when operative in accordance with another embodiment of the present invention;

FIG. 5 schematically illustrates a monitoring system in accordance with a preferred embodiment of the present invention;

Figure 7:
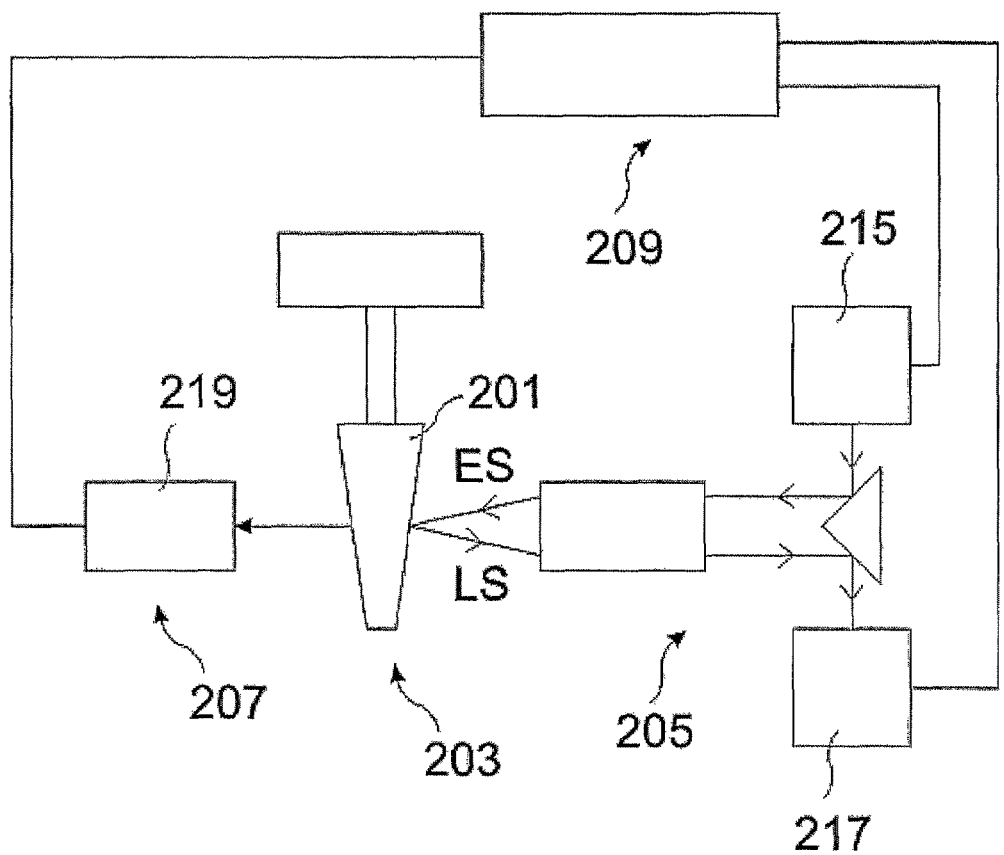
Figure 8:
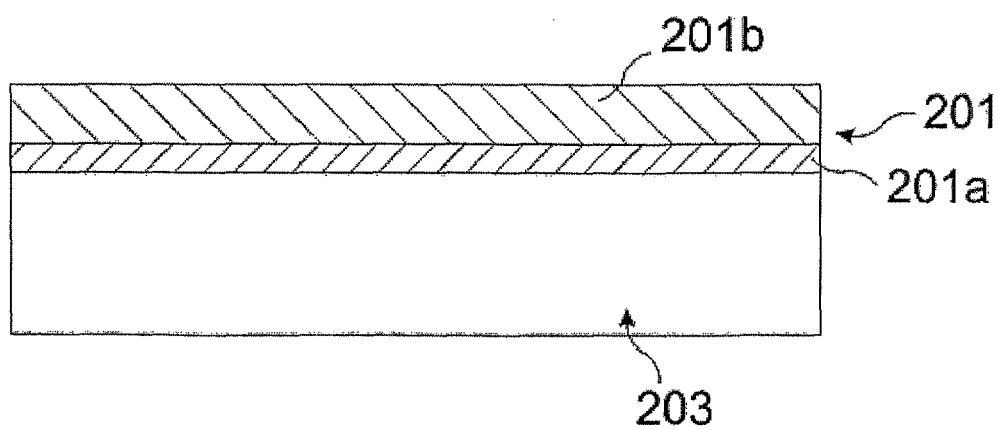

FIG. 7 schematically illustrates a temperature measurement system in accordance with a preferred embodiment of the present invention; and FIG. 8 illustrates an object coated with a TBC in accordance with a preferred embodiment of the present invention.

Figure 1:
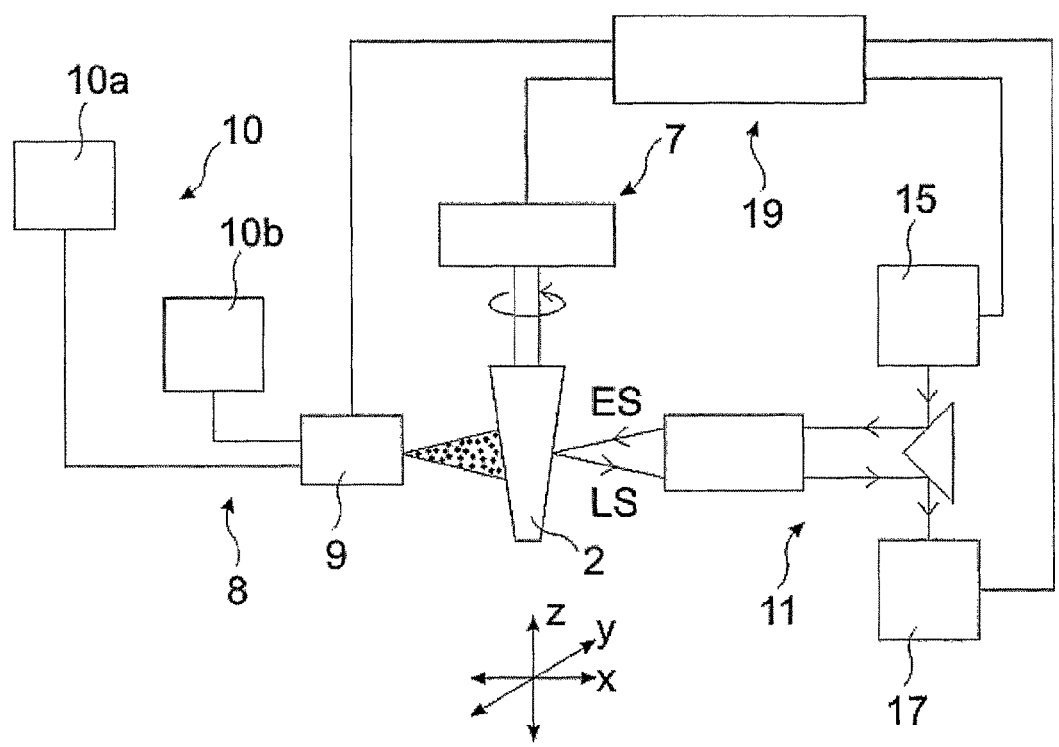

FIG. 1 illustrates a coating system in accordance with a preferred embodiment of the present invention.

The coating system of the present invention provides for the coating of a component 2, for example, in the form of a turbine blade.

As illustrated in FIGS. 2(a) to (e), the component 2 includes a luminescent material 3, in this embodiment as provided in a thin coating 4, at the surface which is to be coated with a structural coating 5. In an alternative embodiment the luminescent material 3 could be incorporated in the component 2.

In one embodiment a bondcoat, for example, of $Al_2O_3$, can be incorporated at the surface of the component 2, such as to promote adhesion of the coatings 4, 5 to the component 2. In one embodiment an $Al_2O_3$ can be formed by thermal growth from an alloy, for example, MCrAlY (where M is a metal), or an intermetallic compound, for example, platinum aluminide.

The coating system comprises a support unit 7 which supports a component 2 which is to be coated. In this embodiment the support unit 7 supports the component 2 in a vertical orient, but in other embodiments the component 2 could be supported in any orient.

In this embodiment the support unit 7 is configured to move the component 2, here rotationally about one axis Z, and translationally in the axes X, Y, Z.

In another embodiment the support unit 7 is configured to hold the component 2 stationary in a fixed position.

The coating system further comprises an applicator unit 8 for applying one or more different coating materials to the surface of the component 2.

The applicator unit 8 includes an applicator head 9 by which a coating material is applied to the component 2, and at least one coating material reservoir 10 for containing at least one coating material.

In this embodiment the applicator head 9 comprises a spray head which delivers a coating material as a spray to the component 2, such as by way of plasma spraying.

In this embodiment the applicator unit 8 comprises a plurality of coating material reservoirs 10a, 10b, each containing a different coating material to be applied to the component 2. As will be described in more detail hereinbelow, in one embodiment, the first coating material reservoir 10a contains a luminescent coating material which is applied first to form the luminescent layer 4 on the surface of the component 2, and the second coating material reservoir 10b contains a structural coating material which is subsequently applied over the luminescent layer 4 to form the structural coating 5 on the component 2.

In this embodiment the applicator head 9 is held stationary in relation to the support unit 7, such that the surface of the component 2 is passed in front of the applicator head 9 to coat the component 2. In this embodiment, as will be described in more detail hereinbelow, a coating of the required thickness is built up by passing the surface of the component 2 a succession of times in front of the applicator head 9.

In an alternative embodiment the applicator head 9 could be moved in relation to the support unit 7, such that the applicator head 9 is moved in relation to the component 2 where either held stationary or moved by the support unit 7.

The coating system further comprises a detector unit 11 for emitting an excitation signal ES to and receiving a luminescence signal LS from the surface of the component 2.

In this embodiment the detector unit 11 comprises a light source 15 which generates a light beam, here a laser beam, as the excitation signal ES and irradiates a point on the surface of the component 2, and a detector 17 which receives the luminescence signal LS from the irradiated surface of the component 2.

With this configuration, as the component 2 is passed in front of the detector unit 11, the surface of the component 2 is scanned by the light beam as generated by the light source 15, such as to map the intensity of the luminescence signal LS from the surface of the component 2.

Figure 3:
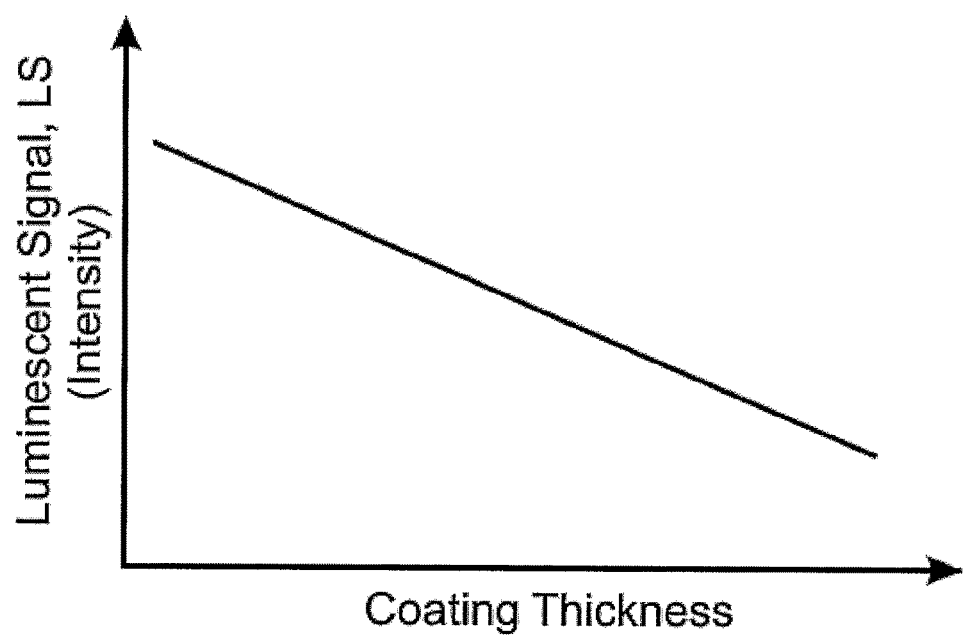

As illustrated in FIG. 3, the intensity of the detected luminescence signal LS is a function of the thickness of the structural coating 5, with the intensity of the luminescence signal LS decreasing as the thickness of the structural coating 5 increases, such that a required thickness of the structural coating 5 corresponds to a predetermined intensity of the luminescence signal LS.

In an alternative embodiment the light source 15 could be configured to irradiate a region of the surface of the component 2, and the detector 17 could comprise a two-dimensional detector array which captures the luminescence signal LS from the irradiated region of the surface of the component 2.

In this embodiment the detector unit 11 includes a calibration reference, which provides at predetermined intervals for measurement at the support unit 7 of the intensity of the light beam as generated by the light source 15, and a condition monitoring module for monitoring the condition of the light beam as generated by the light source 15 during operation of the detector unit 11. Through use of the calibration reference and the condition monitoring module, the intensity of the light beam as generated by the light source 15 can be monitored, such as to provide that the measurement of the thickness of the structural coating 5 is reliable.

The control system further comprises a control unit 19 for controlling the operation of the support unit 7, the applicator unit 8 and the detector unit 11, in this embodiment controlling the operation of the support unit 7 and the applicator unit 8 in response to the luminescence signal LS as detected by the detector unit 11.

Operation of the coating system will now be described hereinbelow.

The component 2 to be coated is firstly mounted in the support unit 7.

Figure 2:
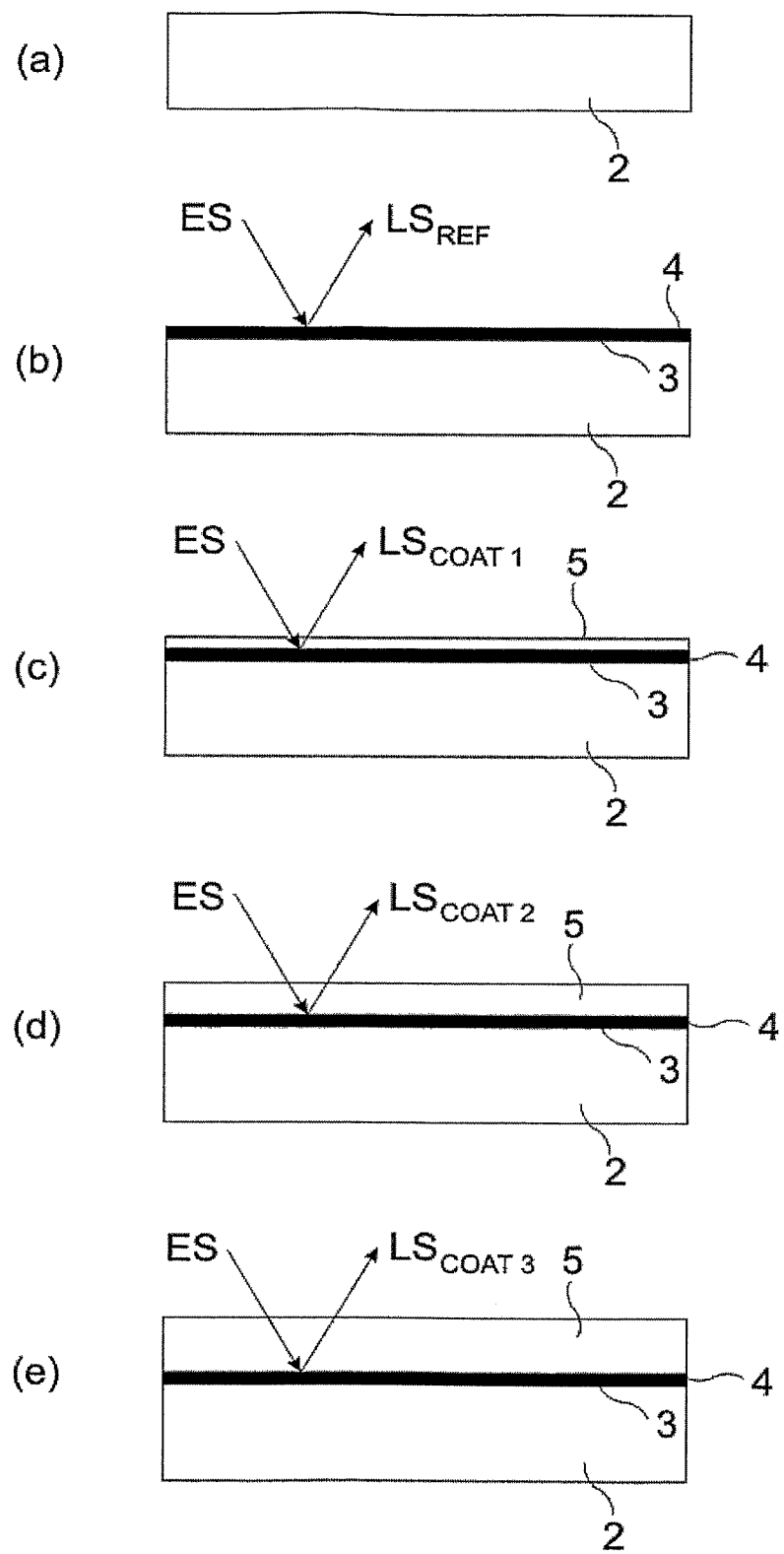

The support unit 7 and the applicator unit 8 are then operated to coat the surface of the component 2 with a luminescent coating 4, as illustrated in FIG. 2(b), in this embodiment by passing the surface of the component 2 in front of the applicator head 9 of the applicator unit 8. In this embodiment the component 2 is coated with a single coat from one pass, but in other embodiments the component 2 could be coated with a plurality of coats from a plurality of passes.

Following coating of the component 2 with the luminescent coating 4, and again as illustrated in FIG. 2(b), the support unit 7 and the detector unit 11 are then operated to map the intensity of the luminescence signal $LS_{REF}$ from the luminescent coating 4 on the surface of the coated component 2.

As will be described further hereinbelow, this mapped intensity of the luminescence signal $LS_{REF}$ from the luminescent coating 4 is utilized as a reference map for the intensity of the luminescence signal $LS_{COAT}$ as subsequently mapped from the luminescent coating 4 during coating of the component 2 with the structural coating 5, and, by reference of the detected luminescence signal $LS_{COAT}$ at given points on the surface of the component 2 to the corresponding points in the reference map of the intensity of the luminescence signal $LS_{REF}$, the thickness of the structural coating 5 can be determined.

The support unit 7, the applicator unit 8 and the detector unit 11 are then operated to coat the surface of the component 2 with a structural coating 5, in this embodiment by moving the surface of the component 2 in front of the applicator head 9 of the applicator unit 8 and coating the component 2 in a plurality of passes, as illustrated in FIGS. 2(c) to (e).

As the structural coating 5 is applied to the component 2, the thickness of which increases following each pass of the applicator head 9, the intensity of luminescence signal $LS_{COAT1}, LS_{COAT2}, \ldots, LS_{COATn}$ from the luminescent coating 4 on the surface of the coated component 2 is continuously mapped and referenced to the datum reference map.

This coating of the component 2 continues until the structural coating 5 is determined to have the required minimum thickness at any point on the surface of the component 2, at which time operation of the support unit 7, the applicator unit 8 and the detector unit 11 is terminated.

In this way, the structural coating 5 has the necessary minimum thickness to provide the required structural function, thus avoiding the need to overcoat the component 2 significantly as would otherwise be necessary to provide that the structural coating 5 is continuous and has the required structural function.

In another embodiment, as a modification of the above-described embodiment, and as illustrated in FIGS. 4(a) to (e), the detector unit 11, instead of being operative to map the luminescence signal $LS_{COAT}$, and hence the thickness of the structural coating 5, during the application of the structural coating 5, can be utilized to determine the thickness of the structural coating 5 following application by the applicator unit 8, such as to determine that the applied structural coating 5 has a minimum thickness at any point on the surface of the component 2.

Operation of the coating system of this embodiment is as follows.

The component 2 to be coated is firstly mounted in the support unit 7.

Figure 4:
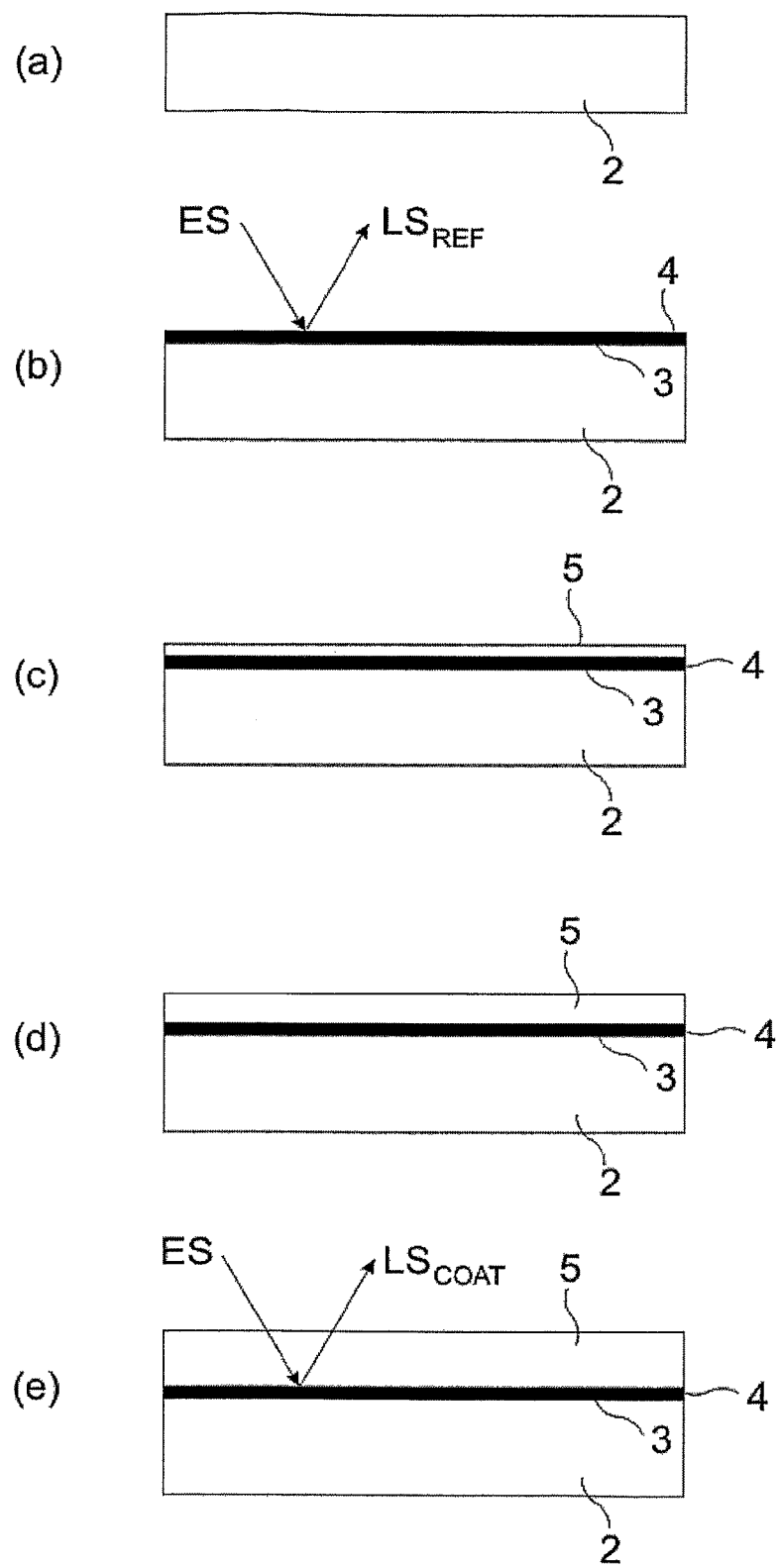

The support unit 7 and the applicator unit 8 are then operated to coat the surface of the component 2 with a luminescent coating 4, as illustrated in FIG. 4(b), in this embodiment by passing the surface of the component 2 in front of the applicator head 9 of the applicator unit 8. In this embodiment the component 2 is coated with a single coat from one pass, but in other embodiments the component 2 could be coated with a plurality of coats from a plurality of passes.

Following coating of the component 2 with the luminescent coating 4, and again as illustrated in FIG. 4(b), the support unit 7 and the detector unit 11 are then operated to map the intensity of luminescence signal $LS_{REF}$ from the luminescent coating 4 on the surface of the component 2.

As described hereinabove, this mapped intensity of the luminescence signal $LS_{REF}$ is utilized as a reference map for the intensity of the luminescence signal $LS_{COAT}$ as subsequently mapped from the luminescent coating 4 following coating of the component 2 with the structural coating 5.

The support unit 7 and the applicator unit 8 are then operated to coat the surface of the component 2 with a structural coating 5 of a desired thickness, in this embodiment by moving the surface of the component 2 in front of the applicator head 9 of the applicator unit 8 and coating the component 2 in a plurality of passes, as illustrated in FIGS. 4(c) to (e).

Following application of the structural coating 5 to the component 2, and again as illustrated in FIG. 4(e), the support unit 7 and the detector unit 11 are then operated to map the intensity of the luminescence signal $LS_{COAT}$ from the luminescent coating 4 on the surface of the coated component 2.

The control unit 19 is then operative to determine the thickness of the structural coating 5 from the mapped intensity of the luminescence signal $LS_{COAT}$ from the luminescent coating 4 on the surface of the coated component 2, by reference of the detected luminescence signal $LS_{COAT}$ at given points on the surface of the component 2 to the corresponding points in the reference map of the intensity of the luminescence signal $LS_{REF}$.

In this way, a determination can be made as to whether the structural coating 5 has the necessary minimum thickness to provide the required structural function, thus avoiding the need to overcoat the component 2 significantly as would otherwise be necessary to provide that the structural coating 5 is continuous and has the required structural function.

Figure 5:
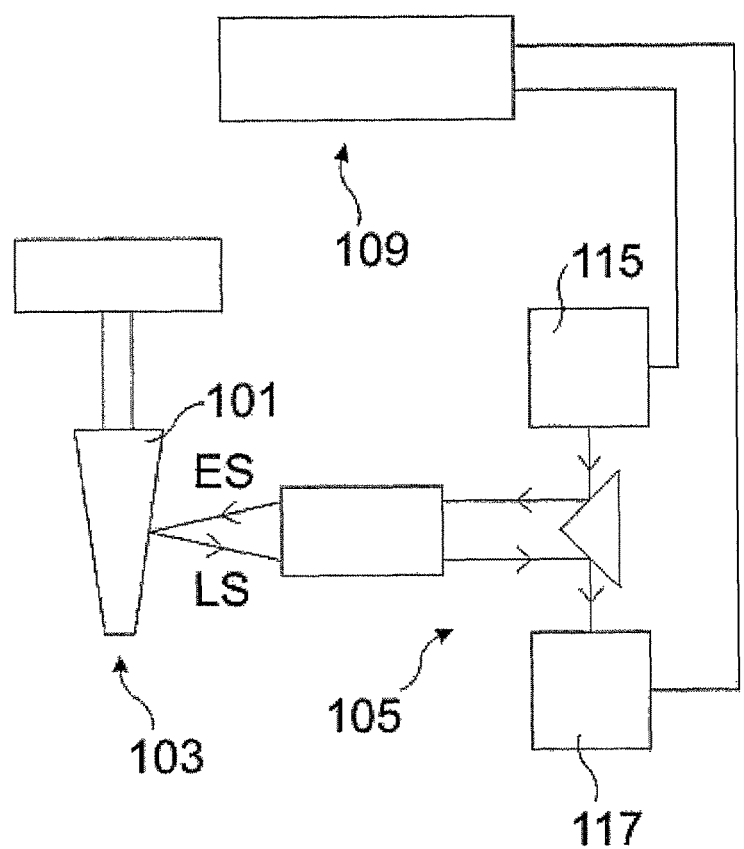

FIG. 5 illustrates a monitoring system for monitoring a TBC 101 as coated on a component 103, which is subjected to a high-temperature environment, for the generation of blisters at the interface of the TBC 101 and the component 103 in accordance with a preferred embodiment of the present invention.

The monitoring system comprises a detector unit 105 for optically detecting a luminescence emission from the TBC 101 as coated on the component 103, and a monitoring unit 109 for monitoring the state of the TBC 101 in response to the detected luminescence emission.

Figure 6A:
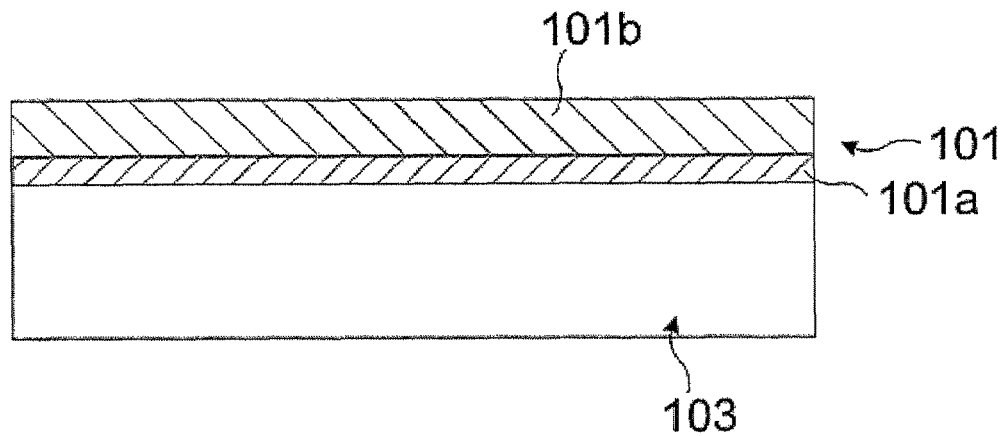
FIG. 6(a) illustrates an object coated with a TBC in accordance with a preferred embodiment of the present invention.

As illustrated in FIG. 6(a), the TBC 101 comprises a first, luminescent coating 101a which is applied to the surface of the component 103, and a second, thicker structural coating 101b which is applied over the surface of the luminescent coating 101a and is such as to allow for the optical interrogation of the luminescent coating 101a.

In this embodiment the luminescent coating 101a is a thin coating as applied to the surface of the component 103, which, while in contact with the surface of the component 103, has a temperature approximately that of the surface of the component 103. As will become apparent hereinbelow, in being a thin coating, the luminescent coating 101a more closely matches the temperature at the surface of the component 103, which is normally at a reduced temperature as compared to the high-temperature, ambient environment.

In one embodiment a bondcoat, for example, of $Al_2O_3$, can be incorporated at the surface of the component 103, such as to promote adhesion of the TBC 101 to the component 103. In one embodiment an $Al_2O_3$ can be formed by thermal growth from an alloy, for example, MCrAlY (where M is a metal), or an intermetallic compound, for example, platinum aluminide.

In one embodiment the luminescent coating 101a has a thickness of up to about 50 μm, preferably up to about 25 μm and more preferably up to about 10 μm.

In one embodiment the luminescent coating 101a comprises a pyrochlore host phase which is doped with at least one luminescent dopant.

Preferably, the at least one luminescent dopant comprises at least one of Pr and Tb.

Preferably, the host phase is doped with between 1 mol % and 10 mol % of the at least one luminescent dopant.

More preferably, the host phase is doped with between 1 mol % and 7 mol % of the at least one luminescent dopant, and in one embodiment between 3 mol % and 7 mol % of the at least one luminescent dopant.

Still more preferably, the host phase is doped with between 4 mol % and 6 mol % of the at least one luminescent dopant.

In a preferred embodiment the host phase is doped with about 5 mol % of the at least one luminescent dopant.

In another embodiment the luminescent coating 101a comprises a zirconia-based host phase and at least one luminescent dopant.

In one embodiment the zirconia-based host phase comprises YSZ, and preferably one of zirconia stabilized with from about 3 mol % to about 6 mol % yttria, more preferably 4 mol % yttria, which is a t' structure, or zirconia stabilized with from about 6 mol % to about 10 mol % yttria, more preferably 8 mol % yttria, which is a cubic structure.

In a further embodiment the zirconia-based host phase comprises a zirconate pyrochlore.

Preferably, the at least one luminescent dopant is at least one element selected from the lanthanide series (rare earth metals).

In one embodiment the at least one luminescent dopant comprises a single dopant selected from Ce, Dy, Er, Eu, Gd, Ho, Nd, Pr, Sm, Tb, Tm and Yb.

In another embodiment the at least one luminescent dopant comprises a pair of dopants selected from the following pairs of elements Gd and Er, Gd and Nd, Gd and Yb, Yb and Nd and Yb and Sm.

In one embodiment the luminescent coating 101a comprises a second, discrete phase.

Preferably, the second phase contains Y and Al.

In one embodiment the second phase includes yttria and an aluminate.

In another embodiment the second phase is a YAG-based phase, and preferably one of $Y_2Al_5O_{12}$ or $Y_3Al_xFe_{5-x}O_{12}$.

In a further embodiment the second phase is a YAP-based phase, and preferably $YAlO_3$.

In one embodiment the second phase is a phase which is chemically and physically stable at high temperatures of typically up to about 1700 C, and preferably when thermally cycled.

In one embodiment the at least one luminescent dopant comprises one or more elements from the lanthanide series, and more preferably one or more elements selected from Ce, Dy, Er, Eu, Gd, Ho, Nd, Pr, Sm, Tb, Tm and Yb.

In a further embodiment the luminescent coating 101a comprises a YAG-based host phase, and preferably one of $Y_2Al_5O_{12}$ or $Y_3Al_xFe_{5-x}O_{12}$, and at least one luminescent dopant In a still further embodiment the luminescent coating 101a comprises a YAP-based host phase, and preferably $YAlO_3$, and at least one luminescent dopant.

In a yet still further embodiment the luminescent coating 101a comprises an yttria host phase and at least one luminescent dopant.

In this embodiment the structural coating 101b is a substantially thicker coating than the luminescent coating 101a, and acts principally as the thermal barrier to the high-temperature, ambient environment.

In one embodiment the structural coating 101b has a thickness of at least about 25 μm, preferably of at least about 50 μm, and more preferably of at least about 100 μm.

In one embodiment the ratio of the thicknesses of the structural coating 101b and the luminescent coating 101a is at least 2:1, preferably at least 5:1, and more preferably at least 10:1.

In one embodiment the structural coating 101b comprises a pyrochlore.

In another embodiment the structural coating 101b comprises a zirconia-based phase.

In one embodiment the zirconia-based phase comprises one of zirconia stabilized with from about 3 mol % to about 6 mol % yttria, preferably 4 mol % yttria, or zirconia stabilized with from about 6 mol % to about 10 mol % yttria, preferably 8 mol % yttria.

In this embodiment the luminescence detector unit 105 comprises a light source 115 which generates a light beam, here a laser beam, as an excitation signal ES which irradiates a region on the surface of the component 103, and a detector 117 which receives a luminescence signal LS from the irradiated surface of the component 103.

With this configuration, the surface of the component 103 is scanned by the light beam as generated by the light source 115, such as to map the luminescence signal LS from the luminescence coating 101a of the TBC 101.

In an alternative embodiment the light source 115 could be configured to irradiate a region of the surface of the component 103, and the detector 117 could comprise a two-dimensional detector array which captures the luminescence signal LS from the irradiated region of the surface of the component 103.

In this embodiment the monitoring unit 109 is operative to monitor the detected luminescence signal LS, which represents the temperature of the luminescent coating 101a over the scanned surface of the component 103, for at least one characteristic which is representative of a temperature transition in the luminescent coating 101a, either in terms of a temperature differential $\Delta T$, in one embodiment between two adjacent locations which would be expected to have a similar temperature, or in terms of a raised absolute temperature $T_R$ as compared to a normal temperature $T_N$.

For as long as the luminescent coating 101a is in contact with the surface of the component 103, as illustrated in FIG. 6(a), the detected luminescence signal LS would have an expected profile.

Figure 6B:
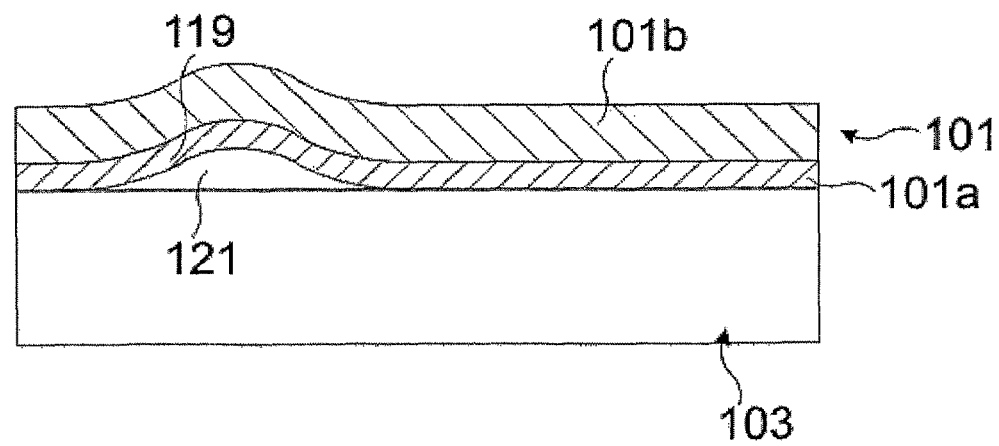
FIG. 6(b) illustrates the object of FIG. 6(a) where including a blister.

However, where a blister 119 develops in the TBC 101, which is such as to generate a void 121 at the interface of the surface of the component 103 and the luminescent coating 101a, as illustrated in FIG. 6(b), the luminescent coating 110a separates from the surface of the component 103 at the localized region of the blister 119, and, as a consequence, has a raised temperature at that localized region when operated in a high-temperature environment, insofar as there is no direct thermal conduction path from that localized region of the luminescent coating 101a, which is thermally connected to the high-temperature environment through the structural coating 101b, and the surface of the component 103, which is at a significantly lower temperature than the environment and would normally provide a thermal conduction path.

This localized increase in the temperature of the luminescent coating 101a is manifested in the detected luminescence signal LS, and can be identified by monitoring the luminescence signal LS for at least one characteristic which is representative of a temperature transition in the luminescent coating 101a, either in terms of a temperature differential $\Delta T$, in one embodiment between two adjacent locations which would be expected to have a similar temperature, or in terms of a raised absolute temperature $T_R$ as compared to a normal temperature $T_N$.

Where the monitoring unit 109 identifies the at least one characteristic in the luminescence signal LS, which is representative of the generation of a blister 119 in the TBC 101, a warning can be provided, and in one embodiment the monitoring unit 109 can provide for the shutting down of the associated machinery.

In one embodiment the luminescent coating 101a can advantageously be formed of luminescent material compositions which are operative to a lower temperature than the high-temperature, ambient environment in which the component 103 is utilized, insofar as the structural coating 101b acts as thermal shield. Furthermore, the luminescent coating 101a could be formed of a luminescent composition which provides a detectable luminescence signal LS at the normal temperature $T_N$ of the luminescent coating 101a, but which does not provide a detectable luminescence signal LS at the raised temperature $T_R$ of the luminescent coating 101a as present at the blister 119.

FIG. 7 illustrates a temperature measurement system for measuring the temperature of a TBC 201 as coated on a component 203, which is subjected to a high-temperature environment, in accordance with a preferred embodiment of the present invention.

The temperature measurement system comprises a luminescence detector 205 for optically detecting a luminescence emission from the component 203, a radiation pyrometer 207 for detecting the radiation emission from the component 203, and a control unit 209 for determining the temperature of the component 203 from the luminescent and radiation emissions as detected by the luminescence detector 205 and the radiation pyrometer 207.

As illustrated in FIG. 8, the TBC 201 comprises a first, luminescent coating 201a which is applied to the surface of the component 203, and a second, thicker structural coating 201b which is applied over the surface of the luminescent coating 201a and is such as to allow for the optical interrogation of the luminescent coating 201a.

In this embodiment the luminescent coating 201a is a thin coating as applied to the surface of the component 203, which has a temperature approximately that of the surface of the component 203.

In an alternative embodiment the TBC 201 could comprise only a single, luminescent coating 201a, which is configured also to provide the necessary structural functionality.

In one embodiment a bondcoat, for example, of $Al_2O_3$, can be incorporated at the surface of the component 203, such as to promote adhesion of the TBC 201 to the component 203. In one embodiment an $Al_2O_3$ can be formed by thermal growth from an alloy, for example, MCrAlY (where M is a metal), or an intermetallic compound, for example, platinum aluminide.

In one embodiment the luminescent coating 201a has a thickness of up to about 50 μm, preferably up to about 25 μm and more preferably up to about 10 μm.

In one embodiment the luminescent coating 201a comprises a pyrochlore host phase which is doped with at least one luminescent dopant.

Preferably, the at least one luminescent dopant comprises at least one of Pr and Tb.

Preferably, the host phase is doped with between 1 mol % and 10 mol % of the at least one luminescent dopant.

More preferably, the host phase is doped with between 1 mol % and 7 mol % of the at least one luminescent dopant, and in one embodiment between 3 mol % and 7 mol % of the at least one luminescent dopant.

Still more preferably, the host phase is doped with between 4 mol % and 6 mol % of the at least one luminescent dopant.

In a preferred embodiment the host phase is doped with about 5 mol % of the at least one luminescent dopant.

In another embodiment the luminescent coating 201a comprises a zirconia-based host phase and at least one luminescent dopant.

In one embodiment the zirconia-based host phase comprises YSZ, and preferably one of zirconia stabilized with from about 3 mol % to about 6 mol % yttria, more preferably 4 mol % yttria, or zirconia stabilized with from about 6 mol % to about 10 mol % yttria, more preferably 8 mol % yttria.

In a further embodiment the zirconia-based host phase comprises a zirconate pyrochlore.

Preferably, the at least one luminescent dopant is at least one element selected from the lanthanide series.

In one embodiment the at least one luminescent dopant comprises a single dopant selected from Ce, Dy, Er, Eu, Gd, Ho, Nd, Pr, Sm, Tb, Tm and Yb.

In another embodiment the at least one luminescent dopant comprises a pair of dopants selected from the following pairs of elements Gd and Er, Gd and Nd, Gd and Yb, Yb and Nd and Yb and Sm.

In one embodiment the luminescent coating 201a comprises a second, discrete phase.

Preferably, the second phase contains Y and Al.

In one embodiment the second phase includes yttria and an aluminate.

In another embodiment the second phase is a YAG-based phase, and preferably one of $Y_2Al_5O_{12}$ or $Y_3Al_xFe_{5-x}O_{12}$.

In a further embodiment the second phase is a YAP-based phase, and preferably $YAlO_3$.

In one embodiment the second phase is a phase which is chemically and physically stable at high temperatures of typically up to about 1700 C, and preferably when thermally cycled.

In one embodiment the at least one luminescent dopant comprises one or more elements from the lanthanide series, and more preferably one or more elements selected from Ce, Dy, Er, Eu, Gd, Ho, Nd, Pr, Sm, Tb, Tm and Yb.

In a further embodiment the luminescent coating 201a comprises a YAP-based host phase, and preferably one of $Y_2Al_5O_{12}$ or $Y_3Al_xFe_{5-x}O_2$, and at least one luminescent dopant.

In a still further embodiment the luminescent coating 201a comprises a YAP-based host phase, and preferably $YAlO_3$, and at least one luminescent dopant.

In a yet still further embodiment the luminescent coating 201a comprises an yttria host phase and at least one luminescent dopant.

In this embodiment the structural coating 201b is a substantially thicker coating than the luminescent coating 201a, and acts principally as the thermal barrier to the high-temperature, ambient environment.

In one embodiment the structural coating 201b has a thickness of at least about 25 μm, preferably of at least about 50 μm, and more preferably of at least about 100 μm.

In one embodiment the ratio of the thicknesses of the structural coating 201b and the luminescent coating 201a is at least 2:1, preferably at least 5:1, and more preferably at least 10:1.

In one embodiment the structural coating 201b comprises a pyrochlore.

In another embodiment the structural coating 201b comprises a zirconia-based phase.

In one embodiment the zirconia-based phase comprises one of zirconia stabilized with from about 3 mol % to about 6 mol % yttria, preferably 4 mol % yttria, or zirconia stabilized with from about 6 mol % to about 10 mol % yttria, preferably 8 mol % yttria.

In this embodiment the luminescence detector unit 205 comprises a light source 215 which generates a light beam, here a laser beam, as an excitation signal ES which irradiates a region on the surface of the component 203, and a detector 217 which receives a luminescence signal LS from the irradiated surface of the component 203. As will be described in more detail hereinbelow, the luminescence detector unit 205 provides for the determination of a reference temperature, which is utilized to calibrate the temperatures as determined from the image as detected by the pyrometer unit 207.

In this embodiment the pyrometer unit 207 comprises a detector 219 which, through focussing optics (not illustrated) detects an image of the radiation, in this embodiment IR radiation, as emitted from the component 203.

Operation of the temperature measurement system is as follows.

The control unit 209 receives an input corresponding to the luminescence signal LS from the luminescence detector unit 205, and an input corresponding to the imaged radiation from the component 203.

The input corresponding to the luminescence signal LS from the luminescence detector unit 205 is utilized to determine a temperature for the irradiated reference region.

The input corresponding to the radiation image from the component 203 is calibrated by determining a calibration factor which provides the section of the imaged radiation which corresponds to the reference region to have the reference temperature, and subsequently applying the reference factor to the radiation image.

With this configuration, the component 203 is pyrometrically mapped in such a manner as to provide absolute temperatures with an accuracy which cannot be achieved by the pyrometer unit 207 alone.

Finally, it will be understood that the present invention has been described in its preferred embodiments and can be modified in many different ways without departing from the scope of the invention as defined by the appended claims.

For example, in one modification, in the monitoring system of FIG. 5, the monitoring unit 109 could be configured to monitor the detected luminescence signal LS for a localized region of reduced absolute temperature $T_R$ as compared to a normal temperature $T_N$, such as would be observed at a blister 119 at the interface of the component 103 and the TBC 101 where operated in an environment which is colder than the temperature of the component 103.

Also, it is to be understood that aspects of any one of the described embodiments can be applied to any of the other described embodiments, for example, in relation to the composition of the structural and luminescent phases.

The invention claimed is:

1. A system for measuring a temperature of an object, the system comprising:
   a luminescence detector unit for detecting a luminescence signal from the object, wherein the object is coated with a thermal barrier coating which includes a luminescent material;
   a radiation pyrometer for detecting an infrared radiation signal from the object, wherein the radiation signal is an image which is captured from the object; and
   a control unit for determining a reference temperature from the luminescence signal and a temperature of the object by calibrating the radiation signal with reference to the reference temperature.

2. The system of claim 1, wherein the thermal barrier coating comprises a first, lower luminescent coating on a surface of the object and a second, upper structural coating on the lower coating.

3. The system of claim 1, wherein the luminescence signal is a luminescence signal from a reference region of the object.

4. A method of measuring a temperature of an object, the method comprising the steps of:
- detecting a luminescence signal from the object, wherein the object is coated with a thermal barrier coating which includes a luminescent material;
- detecting an infrared radiation signal from the object using a radiation pyrometer, wherein the radiation signal is an image which is captured from the object;
- determining a reference temperature from the luminescence signal;
- calibrating the radiation signal with reference to the reference temperature; and
- determining a temperature of the object from the calibrated radiation signal.

5. The method of claim 4, wherein the thermal barrier coating comprises a first, lower luminescent coating on a surface of the object and a second, upper structural coating on the lower coating.

6. The method of claim 4, wherein the luminescence signal is a luminescence signal from a reference region of the object.

* * * * *